United States Patent [19]
LeVeen et al.

[11] Patent Number: 5,573,547
[45] Date of Patent: Nov. 12, 1996

[54] BRUSH FIXATION METHOD FOR ATTACHMENT OF TISSUES AND OCCLUSION OF BLOOD VESSELS

[76] Inventors: Harry H. LeVeen, 321 Confederate Cir.; Eric G. LeVeen, 19 Palmetto Rd., both of Charleston, S.C. 29407; Robert F. LeVeen, 815 S. 94th St., Omaha, Nebr. 68114

[21] Appl. No.: 138,689

[22] Filed: Oct. 19, 1993

[51] Int. Cl.⁶ ............................................. A61B 17/00
[52] U.S. Cl. ............................. 606/232; 606/72; 606/75; 606/151; 606/153; 623/12; 623/13
[58] Field of Search ........................... 606/53, 60, 65, 606/72, 73, 75, 92, 95, 151, 153, 154, 155, 156, 159, 162, 213, 232, 208; 604/52; 623/11, 12, 13; 128/898, 899, 843

[56] References Cited

U.S. PATENT DOCUMENTS

| | | | |
|---|---|---|---|
| 2,143,910 | 1/1939 | Didusch | 606/228 |
| 3,125,095 | 3/1964 | Kaufman et al. | 606/228 |
| 3,687,129 | 8/1972 | Nuwayser | 606/200 |
| 4,990,156 | 2/1991 | Lefebvre | 606/200 |
| 5,037,422 | 8/1991 | Hayhurst et al. | 606/72 |
| 5,061,274 | 10/1991 | Kensey | 606/213 |
| 5,141,520 | 8/1992 | Goble et al. | 606/232 |
| 5,156,606 | 10/1992 | Chin | 606/92 |
| 5,207,679 | 5/1993 | Li | 606/232 |
| 5,318,575 | 6/1994 | Chesterfield | 606/151 |
| 5,380,334 | 1/1995 | Torrie et al. | 606/75 |
| 5,403,346 | 4/1995 | Loeser | 606/228 |

FOREIGN PATENT DOCUMENTS

| | | | |
|---|---|---|---|
| 604145 | 10/1934 | Germany | 606/162 |
| 0095459 | 4/1939 | Switzerland | 606/159 |
| 1568999 | 6/1990 | U.S.S.R. | 606/73 |
| WO93/16650 | 9/1993 | WIPO | 606/151 |

*Primary Examiner*—Michael Powell Buiz
*Assistant Examiner*—Jeffrey A. Schmidt
*Attorney, Agent, or Firm*—Herbert F. Ruschmann; Lawrence I. Wechsler

[57] ABSTRACT

A method of fixation for use within animal and human bodies provides for the insertion of brushes, of cylindrical and conical designs, into openings wherein bristles of the brushes are deflected by walls of the openings such that the brushes are locked in place and resist forces applied thereto. An embodiment of the invention includes boring a hole into a cancellous bone structure and inserting a brush into the hole. The hole is of a smaller diameter than the brush and is locked in the hole by the bristles. Tissue, such as tendon, may then be attached to material affixed to an end of the brush. Another embodiment of the method includes insertion of a brush into a blood vessel such that the blood flow is either occluded or strained by the bristles of the brush.

39 Claims, 4 Drawing Sheets

BRUSH FIXATION METHOD FOR ATTACHMENT OF TISSUES AND OCCLUSION OF BLOOD VESSELS

BACKGROUND OF THE INVENTION

The present invention relates to a method for the attachment of tissues, and more particularly, to a method wherein a cylindrical brush structure is inserted into a hole bored in bone and tissue, such as tendon, is attached to an exposed end of the brush structure. Additionally, the method provides for the occluding of blood vessels by means of the insertion of appropriate brush devices.

During surgery it is necessary to attach, or fixate, tissues to one another where the tissues are of both similar and dissimilar types. Conventional methods include suturing and stapling soft tissues together. These methods however are not suitable for attachment of soft tissues to bone. Due to its rigid composition, suturing is not possible and staples pull free as they are worked loose by repetitive application of stresses.

Special screws and other fixation devices for making attachments to bone have been devised. However, these devices are not easily adapted to the reattachment of tendons which are torn from their points of insertion in the bone, for instance, where small tendons in the fingers are to be reattached to phalanges. Fixation devices for the attachment of tendons in bone should be fabricated of a material that is absorbable in the body. Stress points from resulting from non-absorbable fixation devices, such as screws, bring about bone reabsorption and local necrosis. Such occurrences eventually lead to failure of a repair effected using non-absorbable fixation devices. Therefore, such devices must be removed by a surgeon at a later date. Thus, a need exists for a fixation method permitting absorbable materials to be used in affixing tissues to bone.

Vascular surgery presents a need for an occlusive device which may be inserted into an open blood vessel. For instance, back bleeding from small blood vessels arising from an aorta can be exceedingly troublesome during surgery for an aortic aneurysm. Conventional methods of clamping the vessels are inconvenient or impracticable in certain situations. Therefore, a need exists for a device which can be inserted inside a blood vessel to plug it. Similarly, vascular surgery requires devices that can be inserted into a blood vessel to prevent blood clots from passing therethrough. For example, devices are presently used to prevent large blood clots from passing through a vena cava vein and causing pulmonary emboli. The devices presently employed are prone to dislodging and passing through a dilated vena cava vein. Therefore, there is a need for improved fixation methods used in vascular surgery.

SUMMARY OF THE INVENTION

Accordingly, it is an object of the invention to provide a method of fixation within animal and human bodies which overcomes the drawbacks of the prior art.

It is a further object of the invention to provide a method of fixating tissue to bone with minimal effort.

It is a still further object of the invention to provide a method of fixation for the fixating of tissues to bone wherein pressure points upon the bone are minimized.

Another object of the present invention is to provide a method of fixation wherein a fixation device is completely biodegradable thus eliminating a need for later removal.

Yet another object of the present invention is to provide a method for the occlusion of a blood vessel wherein the risk of embolization of an occlusion device is minimized.

Still another object of the present invention is to provide a method for the occlusion of a blood vessel by means of insertion of an occluding device into the blood vessel wherein the occluding device is retained in place by deflected bristles.

A particular object of the present invention is to provide a method using an occluding device for occluding blood vessel which is adaptable to blood vessels of varying sizes.

Another particular object of the present invention is to provide a method for straining a flow of blood within a blood vessel so as to prevent the passage of blood clots.

Briefly stated, there is provided a method of fixation for use within animal and human bodies which provides for the insertion of brushes, of cylindrical and conical designs, into openings wherein bristles of the brushes are deflected by walls of the openings such that the brushes are locked in place and resist forces applied thereto. An embodiment of the invention includes boring a hole into a cancellous bone structure and inserting a brush into the hole. The hole is of a smaller diameter than the brush and is locked in the hole by the bristles. Tissue, such as tendon, may then be attached to material affixed to an end of the brush. Another embodiment of the method includes insertion of a brush into a blood vessel such that the blood flow is either occluded or strained by the bristles of the brush.

Features of the present invention include a method of fixation for use within a body of an animal, including a human, comprising: the body having a hole; and inserting a brush having bristles into the hole of the body such that the bristles deflect and lock the brush in the hole.

Particular features of the present invention include the brush having an attachment means including: a cloth strip for affixing tissue thereto; a loop for affixing the tissue; wires extending from a stem of the brush for affixing the tissue to the brush by sewing the extended wires through the tissue; additionally the stem optionally has a sharpened cutting end for boring into bone.

Another feature of the present invention includes a method of fixating tissue to a bone within a body of an animal, including a human, comprising: boring a hole in the bone; inserting a brush having bristles into the hole such that the bristles deflect and lock the brush in the hole; the brush having an the attachment means including a cloth strip; and affixing the tissue to the cloth strip.

Yet another feature of the present invention includes a method of interrupting a flow of blood in blood vessels in an animal, including a human, comprising: transecting a blood vessel; inserting a brush having bristles into the blood vessel such that the bristles deflect and lock the brush in the blood vessel; and the bristles being space apart such that the blood flow is one of substantially stopped by accumulation of clots upon the bristles and strained for clots by the bristles. Optionally, the method includes further features wherein the brush is contained in a retaining tube with a first set of the bristles being deflected in a first direction and a second set of the bristles being deflected in a second direction opposing the first direction; inserting the brush includes inserting retaining tube, with the brush therein, into the blood vessel such that the brush is position at a desired point in the blood vessel; and withdrawing the retaining tube while keeping the brush at the desired position by applying force to the brush.

Still another feature of the present invention is an apparatus for insertion into a blood vessel for the purpose of interrupting a flow of blood therein comprising: a brush having a substantially cylindrical shape; the brush being contained in a retaining tube such that a first set of bristles is deflected in a first direction and a second set of bristles is deflected in a second direction opposing the first direction; and bristles of the first and second sets of bristles being space apart such that the blood flow is one of substantially stopped by accumulation of clots upon the bristles and strained for clots by the bristles.

These and other objects, features and advantages of the present invention will become apparent from the following description read in conjunction with the accompanying drawings, in which like reference numerals designate the same elements.

DETAILED DESCRIPTION OF PREFERRED EMBODIMENTS

Figure 1:
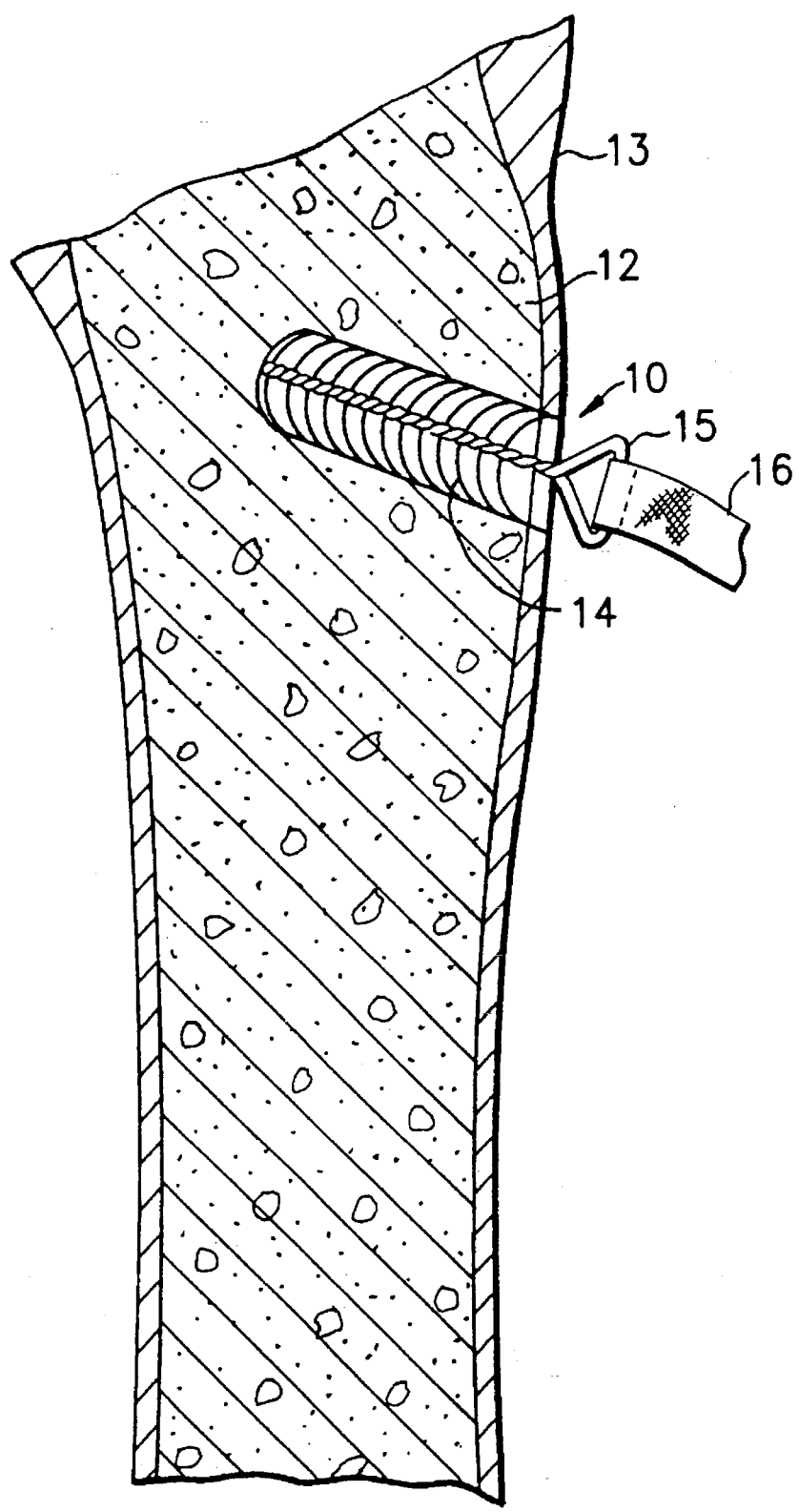
FIG. 1 is a cross section view of a fixation device fixated within cancellous bone according to the present invention.

Referring to FIG. 1, a method of fixation include inserting a fixation device 10, comprising a cylindrical brush, into a hole bored into a cancellous bone portion 12 of a bone 13. Bristles 14 of the fixation device 10 are deflected by the cancellous bone 12 during insertion of the fixation device 10 into the hole. A diameter of the hole is chosen such that the bristles 14 are bent through an angle of 30° to 60°. An attachment loop 15 has a cloth strip 16 affixed thereto. A tendon (not shown) is sutured to the cloth strip 16 and thus held in contact with and fixated to the bone 13.

Alternatively, the tendon may be attached to the cloth strip 16 prior to insertion and the fixation device 10 may be inserted with the attachment loop 15 proceeding first into the hole. In such a insertion method some bristles are obstructed from making contact with the cancellous bone 12 by the cloth strip 16. However, force exerted upon the fixation device 10 is primarily in a direction opposing that of insertion wherein pressure is evenly distributed by the bristles 14 which are making contact with the cancellous bone 12.

Referring again to FIG. 1, the bristles 14 exert an outward pressure against a rough interior hole surface of the cancellous bone portion 12, and distribute stresses applied to the fixation device 10 via the tendon throughout the hole. The bristles 14 thus lock the fixation device 10 in place and prevent a creation of localized areas of stress on the bone 13 experienced when metal screws are used. Furthermore, the method obviates the need to screw prior art devices into a hole and replaces the effort with one of mere insertion by means of pressure applied to the fixation device 10.

Figure 2A:
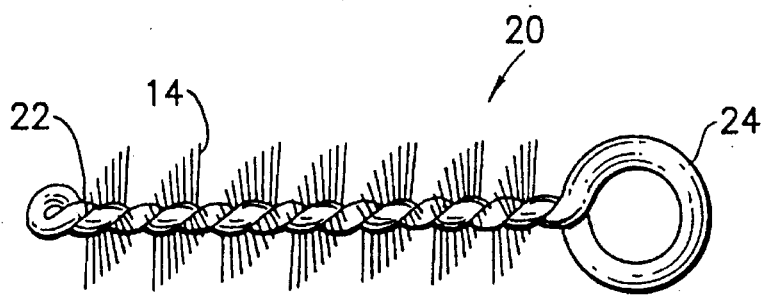
FIG. 2a is a plan view of a fixation device of the present invention having a loop.
Figure 2B:
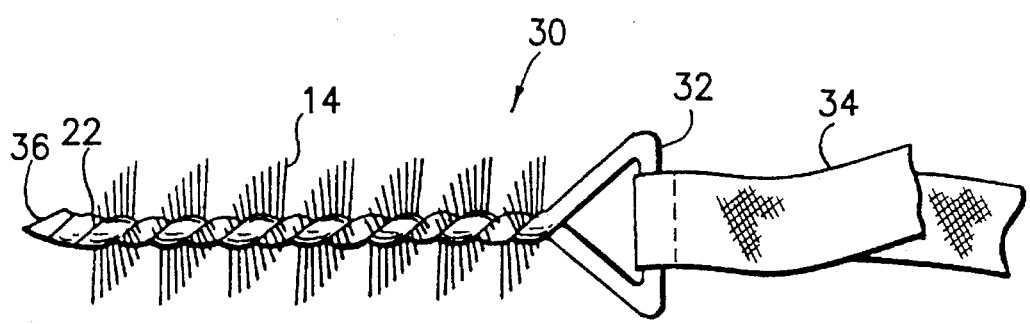
FIG. 2b is a plan view of the fixation device of FIG. 1 having a cloth strip attachment means.

Referring to FIGS. 2a–2b, various embodiments of the fixation device of the present invention are shown. In FIG. 1a a fixation device 20 has the bristles 14 extending outwardly at right angles from a stem 22. The stem 22 is terminated in a generally circular attachment loop 24 to which tissues may be directly sutured. The bristles 14 are flexible yet relatively stiff, possessing a high modulus of elasticity which allows sufficient pressure to be exerted by the bristles 14 when bent through an angle of 30° to 60° so that the fixation device 20 locks into place. The tensile strength of a union between the fixation device 20 and a bone is superior to other methods now in use when the fixation device 20 is inserted into a hole of the prescribed diameter. The numerous bristles 14 engage a large surface area of bone (as shown in FIG. 1) and cushion applications of stress by virtue of their elastomeric properties.

Figure 2C:
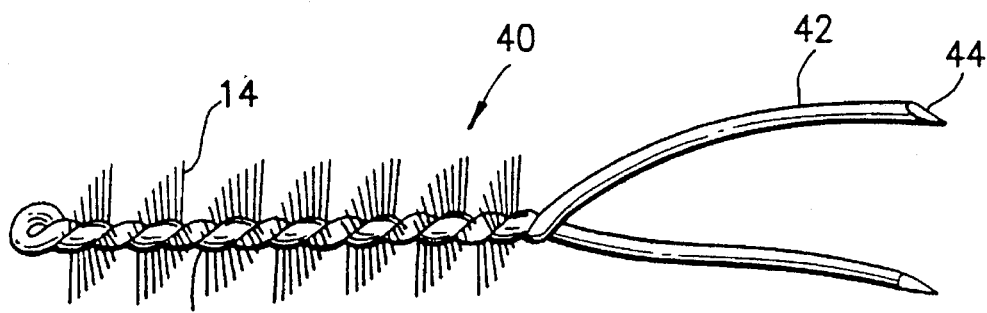
FIG. 2c is a plan view of a fixation device of the present invention having extended wires with sharpened ends as an attachment means.

In FIGS. 2a–2c, the bristles 14 and the stem 22 may be formed of various materials dependent upon whether fixation devices 20, 30, 40, are desired to be biodegradable or non-biodegradable. For instance, the bristles 14 may be formed from oriented nylon which is biodegradable or from polyester which resists biodegradation. The stem 22 may be formed from such plastics or alternatively, it may be formed from stainless steel or titanium wire. The bristles 14 may also be formed of such materials where biodegradability is not required. Preferred embodiments of the present invention include having the stem 22 formed from twisted stainless steel wire and the bristles 14 formed from a polyamide or a polyester.

Referring to FIG. 2b, a fixation device 30 has a flattened loop 32 through which a cloth strip 34 is affixed. The flattened loop 32 distributes stress evenly over a width of the cloth strip 34. A tendon (not shown) is sutured to the cloth strip 34 as noted above. Suturing over a surface area of the cloth strip 34 permits stress to be distributed over the surface area of the cloth strip 34 and the tendon sutured to it. The stem 22 optionally has a cutting point 36, similar to that used in Kirschner wire employed in orthopedic surgery, which is used to bore into a bone and obviate the need to bore a hole with a drill. Angular motion boring into a section of cancellous bone is effective in opening a hole of sufficient diameter for the bristles 14 to lock into.

The cloth strip 34 is woven from fibers of polytetrafloroethylene (Teflon), polyester (Dacron), or other non-absorbable material to which tendons are sewn. Alternatively, an absorbable material may be used where required by the application.

Referring to FIG. 2c, a fixation device 40 has extended wires 42 with sharpened ends 44. The extended wires 40 are inserted through tissue to be affixed and tied or twisted together. Excess length of the extended wires 40 is then cut off.

Figure 3A:
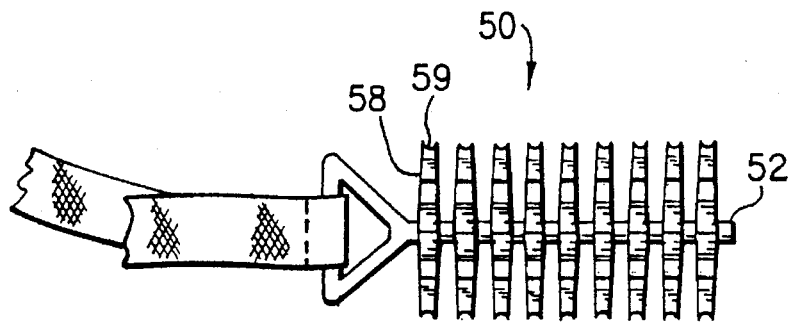
FIG. 3a is a side plan view of a fixation device of the present invention which is formed of plastic.
Figure 3B:
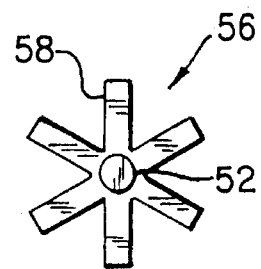
FIG. 3b is an end view of the fixation device of FIG. 3a showing a star shaped bristle configuration.

Referring to FIGS. 3a and 3b, another embodiment of the present invention includes a fixation device 50 which is formed entirely of plastic. Thus, the entire device may be completely absorbable, i.e. biodegradable, in the human body. One particularly suitable plastic is polyglycolic acid which is a aliphatic straight chain polyester which body tissues can absorb and degrade. Polylactide is another plastic which is biodegradable in the body. Nylon, a polyamide, can also be broken down by the body by amidases over a long period of time.

The fixation device 50 may be manufactured from star shaped plastic sections 56 fused upon a plastic stem 54. The star shaped plastic sections 56 have star bristles 58 separated by a sufficient angle such that they deflect 30° to 60° when inserted in a hole. The 30° to 60° range is an optimal range and it is recognized the other ranges of deflection are effective. The star bristles 58 optionally have concaved ends 59 which improve retention strength when the fixation device 50 is inserted in the hole. Alternatively, a molding or an individual bristle insertion method of manufacture is used when the stem 22 is composed of solid plastic.

Figure 4:
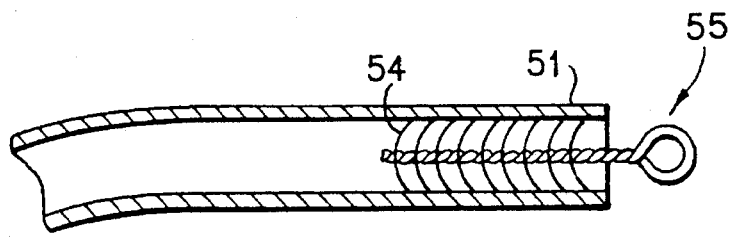
FIG. 4 is a cross section view of the fixation device of FIG. 2a inserted into a blood vessel according to another embodiment of the present invention.

Referring to FIG. 4 a cylindrical brush 50 may also be employed as tamponading or screening devices in vascular surgery. While bleeding from blood vessels is generally arrested during surgery by means of vascular clamps, it is often desirable to occlude a blood vessel internally. For instance, during surgery for the correction of an aneurysm, back bleeding from lumbar arteries is troublesome. Such bleeding may be controlled by inserting the cylindrical brush 50 into an opening of a transacted lumbar artery 52. The cylindrical brush 50 is inserted in a direction opposing a flow of blood in the lumbar artery 52 such that a pressure of blood flow is opposed by a locking force of deflected bristles 54. If the cylindrical brush 50 is inserted in a direction of the blood flow it will embolize. The deflected bristles 54 act as a web upon which the blood clots and occludes the lumbar artery 52. In such an application, the deflected bristles 54 are formed from a material of sufficient resiliency so as to retain the cylindrical brush in place against the pressure of blood flow while allowing removal without damaging the lumbar artery 52. Additionally, the material may be chosen for its thrombogenic properties.

Figure 5:
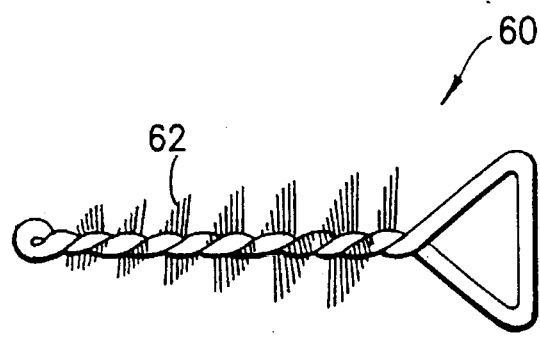
FIG. 5 is a side plan view of a tapered fixation device of another embodiment of the present invention.

Referring to FIG. 5, another embodiment of a device used in the present invention includes a conical brush 60 having bristles 62 which have varying lengths forming a taper. The conical brush 60 is equally suitable for use in tamponading blood vessels. The taper of the bristles 62 allows the conical brush 60 to be used to occlude blood vessels of varying diameters. The conical brush 60 is inserted a requisite distance into a blood vessel so that bristles 62 of a sufficient length engage an interior of the blood vessel and lock the conical brush 60 in place.

Figure 6A:
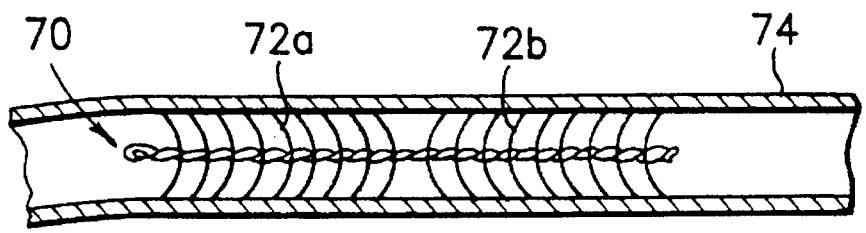
FIG. 6a is a cross section view of another fixation device, inserted in a blood vessel, having bidirectionally deflected bristles according to yet another embodiment of the present invention.
Figure 6B:
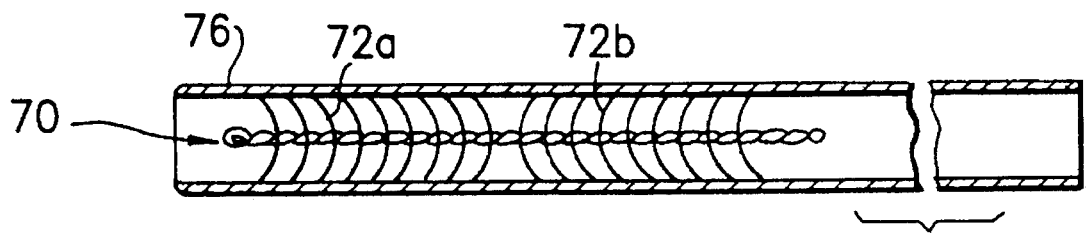
FIG. 6b is a cross section view of the fixation device of FIG. 6a in a retaining tube according to the present invention.

Referring to FIGS. 6a and 6b, another embodiment of a device used in the method of the present invention is shown wherein a cylindrical brush serves as an occlusion device 70 suitable for bidirectional use. The occlusion device 70 has a first set of deflected bristles 72a deflected in a first direction and a second set of deflected bristles 72b deflected in a second direction opposing the first direction. In FIG. 6a, the occlusion device 70 is shown inserted in a blood vessel 74. Bristles 72a and 72b serve to lock the bidirectional occlusion device 70 in the blood vessel 74 so as to oppose fluid flow in either direction. In FIG. 6b, the occlusion device 70 is shown packaged in a retaining tube 76. The retaining tube 76 serves to keep the bristles, 72a and 72b, in a pre-deflected position prior to insertion in the blood vessel 74. An outer diameter of the retaining tube 76 is smaller than an inner diameter of the blood vessel 74.

The bidirectional occlusion device 70 is used in applications where a vessel is subject to fluid flow in either direction. In one such situation, anglographers occlude a splenic artery in cirrhotics with portal hypertension. The method of occlusion of the present invention includes the placement of the occlusion device 70 at a proper point in the vessel while still contained within the retaining tube 76. The retaining tube 76 may be of varying lengths to facilitate proper placement of the occlusion device 70. Once properly placed, the occlusion device is extracted from the retaining tube 76 by withdrawing the retaining tube 76 while the occlusion device 70 is maintained in position relative to the vessel by means of a rod (not shown) inserted within the retaining tube 76. Once the bidirectional occlusion device is free of the retaining tube 76, both the rod and the retaining tube 76 are removed from the vessel.

In a preferred embodiment, the retaining tube 76 is formed of polished stainless steel. The smooth surface of the polished stainless steel permits sliding of the bristles, 72a and 72b, without the application of excessive force. Packaging the occlusion device 70 in the retaining tube 76 is accomplished by first inserting the occlusion device 70 in the retaining tube 74 in a first direction such that the occlusion device 70 protrudes from an end of the retaining tube opposing an insertion end. The occlusion device 70 is then withdrawn within the retaining tube 74 resulting in the deflection of the bristles, 72a and 72b, in opposing directions.

Another embodiment of the present invention includes a method for straining blood flow in a vessel. In particular, a straining device, similar to the occlusion device 70, is inserted into a vena cava to strain out clots so as to prevent pulmonary emboli. In such an application, the straining device is constructed the same as the occlusion device 70 except that the bristles, 72a and 72b, are less numerous thereby acting as a strainer instead of a plug.

In the present disclosure various arteries and veins are referred to for the purpose illustrations, representing tubular structures and particular applications, and not as limitations. Additionally, those skilled in the art having the benefit of this disclosure will recognize that other materials consistent with a desired degree of biodegradability and elasticity may be employed. The application of such materials is considered to be within the scope and spirit of the present invention.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A device for fixing a tissue to a bone, comprising;
   a brush including first and second ends;
   said brush further including a stem and a plurality of elongated bristles attached to said stem in a spaced apart manner over at least a portion of a length thereof, said plurality of elongated bristles arranged crosswise to said stem, an average distance between ends of opposed ones of said plurality of elongated bristles defining a brush diameter;
   said brush further including means for permitting resilient angular deflection of at least end portions of said plurality of elongated bristles away from an original orientation thereof, such that when said brush is inserted into a receiving hole in the bone, the receiving hole having a diameter less than said brush, said at least end portions of said plurality of elongated bristles are angularly deflected in a direction opposite a direction of insertion; and a cloth in captive engagement with said first end of said brush and extending therefrom, at least a portion of said cloth including a widened surface for receiving the tissue in overlapping engagement therewith, for joining of the tissue and said cloth, one to the other.

2. A device according to claim 1, wherein said plurality of bristles are arranged in spiral fashion around said stem.

3. A device according to claim 1, wherein said means for permitting resilient angular deflection of at least end portions of said plurality of elongated bristles includes said plurality of elongated bristles being formed from a resilient material to permit bending thereof.

4. A device for fixing tissue to a bone, comprising;

a brush including first and second ends;

said brush further including a stem and a plurality of elongated bristles attached to said stem in a spaced apart manner over at least a portion of a length thereof, said plurality of elongated bristles arranged crosswise to said stem, an average distance between ends of opposed ones of said plurality of elongated bristles defining a brush diameter;

said brush further including means for permitting resilient angular deflection of at least end portions of said plurality of elongated bristles away from an original orientation thereof such that when said brush is inserted into a receiving hole in the bone, the receiving hole having a diameter less than said brush, said at least end portions of said plurality of elongated bristles are angularly deflected in a direction opposite a direction of insertion;

a cloth in captive engagement with said first end of said brush and extending therefrom, at least a portion of said cloth including a widened surface for receiving the tissue in overlapping engagement therewith, for attachment of the tissue thereto; and a cutting point carried on said brush at said second end for permitting formation of the receiving hole by angular boring motion thereof.

5. A device for fixing a tissue to a bone, comprising;

a brush including first and second ends;

said brush further including a stem and a plurality of elongated bristles attached to said stem in a spaced apart manner over at least a portion of a length thereof, said plurality of elongated bristles arranged crosswise to said stem, an average distance between ends of opposed ones of said plurality of elongated bristles defining a brush diameter;

said brush further including means for permitting resilient angular deflection of at least end portions of said plurality of elongated bristles away from an original orientation thereof, such that when said brush is inserted into a receiving hole in the bone, the receiving hole having a diameter less than said brush, said at least end portions of said plurality of elongated bristles are angularly deflected in a direction opposite a direction of insertion;

means for attaching the tissue to said first end of said brush; and a cutting point carried on said brush at said second end for permitting formation of the hole by angular boring motion thereof.

6. A device according to claim 5, wherein said plurality of bristles are arranged in spiral fashion around said stem.

7. A device according to claim 5, wherein said means for permitting resilient angular deflection of at least end portions of said plurality of elongated bristles includes said plurality of elongated bristles being formed from a resilient material to permit bending thereof.

8. A device for fixing a tissue to a bone, comprising;

a brush;

said brush including a stem and a plurality of elongated bristles attached to said stem in a spaced apart manner over at least a portion of a length thereof, said plurality of elongated bristles arranged crosswise to said stem, an average distance between ends of opposed ones of said plurality of elongated bristles defining a brush diameter;

said brush further including means for permitting resilient angular deflection of at least end portions of said plurality of elongated bristles away from an original orientation thereof, such that when said brush is inserted into a receiving hole in the bone, the receiving hole having a diameter less than said brush, said at least end portions of said plurality of elongated bristles are angularly deflected in a direction opposite a direction of insertion;

at least a portion of said plurality of elongated bristles being comprised of a resilient material, said at least a portion of said plurality of elongated bristles further including concave end surfaces at free ends thereof; and means for attaching the tissue to said brush.

9. A device, according to claim 8, wherein said brush is comprised entirely of a biodegradable plastic.

10. A device for insertion into a vessel subject to bidirectional fluid flow for occlusion thereof, the device comprising:

a tube having an external diameter smaller than an internal diameter of the vessel;

a brush including first and second ends;

said brush further including a stem and a plurality of elongated bristles attached in crosswise manner to said stem spaced apart over at least a portion of a length thereof, an average distance between ends of opposed ones of said plurality of elongated bristles defining a brush diameter, said brush diameter being larger than said internal diameter of the vessel;

said brush further including means for permitting resilient angular deflection of at least end portions of said plurality of elongated bristles away from an original orientation thereof;

said brush being disposed within said tube with a first portion of said plurality of elongated bristles disposed between said first end and an intermediate position between said first and second ends being deflected at least at said end portions thereof in a first direction towards said first end; and a second portion of said plurality of elongated bristles disposed between said intermediate position and said second end being deflected at least at said end portions thereof in a second direction towards said second end.

11. A device according to claim 10, wherein said means for permitting resilient angular deflection of at least end portions of said plurality of elongated bristles includes said plurality of elongated bristles being formed from a resilient material to permit bending thereof.

12. A device according to claim 10, wherein said tube is comprised of polished stainless steel.

13. A device for fixing a tissue to a bone, comprising;

a brush;

said brush including at least two wires including first and second portions, said at least two wires being laterally joined over a length of said first portions to define at least in part a stem, said at least two wires further including second portions, each of said second portions separately extending from a common end of said stem said brush further including a plurality of elongated bristles attached to said stem in a spaced apart manner over at least a portion of a length thereof, said plurality of elongated bristles arranged crosswise to said stem, an average distance between ends of opposed ones of said plurality of elongated bristles defining a brush diameter;

said brush further including means for permitting resilient angular deflection of at least end portions of said plurality of elongated bristles away from an original orientation thereof, such that when said brush is inserted into a receiving hole in the bone, the receiving hole having a diameter less than said brush, said at least end portions of said plurality of elongated bristles are angularly deflected in a direction opposite a direction of insertion; and said second portions of said at least two wires being tapered at free ends thereof to present sharpened ends, said second portions further having sufficient rigidity to permit a piercing of the tissue by the sharpened ends of said second portions without requiring use of needles.

14. A device for fixing a tissue to a bone, comprising;

a brush including first and second ends;

said brush further including a stem and a plurality of elongated bristles attached to said stem in a spaced apart manner over at least a portion of a length thereof, said plurality of elongated bristles arranged crosswise to said stem, an average distance between ends of opposed ones of said plurality of elongated bristles defining a tapered bristle portion having a brush diameter which tapers in a direction from said first end to said second end;

said brush further including means for permitting resilient angular deflection of at least end portions of said plurality of elongated bristles away from an original orientation thereof, such that when said second end of said brush is inserted into a receiving hole in the bone, the receiving hole having a diameter less than that of at least a portion of said tapered bristle portion, said at least end portions of said plurality of elongated bristles over said at least a portion of said bristle portion are angularly deflected in a direction opposite a direction of insertion; and means for attaching the tissue to said brush carried on said first end of said brush.

15. A method of fixation for use within a body of an animal, including a human, to fixate a tissue to a bone comprising:

providing a brush having a stem with a first and a second end, and bristles, disposed substantially continuously from said first end to said second end;

said bristles extending radially from said stem defining a brush diameter determined by a distance between ends of radially opposing ones of said bristles;

boring a hole in the bone with a diameter less than said brush diameter;.

inserting said brush into said hole such that said bristles deflect an angular amount sufficient to lock said brush in said hole by exerting forces substantially uniformly against an interior surface of said hole;

said brush having an attachment means for attaching the tissue at said first end of said brush; and connecting the tissue to said brush via said attachment means.

16. A method, according to claim 15, comprising:

said attachment means including a cloth strip; and affixing the tissue to said cloth strip.

17. A method, according to claim 15, comprising:

said attachment means including a loop; and affixing said tissue to said loop.

18. A method, according to claim 15, comprising:

said attachment means including wires having sharpened ends extending from said stem of said brush; and affixing said tissue to said brush by piercing the tissue with said sharpened ends of said extended wires.

19. A method, according to claim 15, comprising:

said stem having a sharpened cutting end at said second end; and said boring being effected by inserting said sharpened cutting end into said bone while rotating and angularly moving said brush.

20. A method, according to claim 15, comprising said bristles being formed of a plastic selected from a group comprising polyester, nylon, polytetrafluoroethylene, polyglycolic acid, and polylactide.

21. A method, according to claim 15, said stem being formed of a plastic selected from a group comprising polyester, nylon, polytetraflouroethylene, polyglycolic acid, and polylactide.

22. A method, according to claim 15, comprising:

Said stem being formed of a metal selected from a group comprising stainless steel, titanium, and tantalum.

23. A method, according to claim 15, comprising said brush being formed entirely of a biodegradable plastic.

24. A method of fixing a tissue to a bone within a body of an animal, including a human, comprising:

boring a hole in the bone;

inserting a brush having bristles into said hole such that said bristles deflect and lock said brush in said hole, said brush having an attachment means including a cloth strip having at least in part a widened dimension;

positioning said tissue in overlapping engagement with said cloth strip; and joining the tissue and said cloth strip, one to the other, across said widened dimension.

25. A method of fixing a tissue to a bone within a body of an animal, including a human, comprising:

boring a hole in the bone;

inserting a brush having bristles into said hole such that said bristles deflect and lock said brush in said hole, said bristles deflecting an angular amount sufficient to lock said brush in said hole by exerting forces substantially uniformly against an interior surface of said hole;

said brush having an attachment means including a cloth strip; and affixing the tissue to said cloth strip.

26. A method for fixing a tissue to a bone, comprising the steps of:

providing a brush, said brush including a stem and a plurality of elongated bristles attached to said stem in a spaced apart manner over at least a portion of a length thereof, said stem having a stem diameter defined by an average cross-sectional width thereof, said plurality of elongated bristles arranged crosswise to said stem, an average distance between ends of opposed ones of said plurality of elongated bristles defining a brush diameter, said brush diameter being substantially greater than said stem diameter, said brush including means for permitting resilient angular deflection of at least end portions of said plurality of elongated bristles away from an original orientation thereof;

boring a hole in the bone, said hole having a diameter less than said brush diameter and a depth sufficient to receive said brush substantially therein;

inserting said brush into said hole with said stem in substantial alignment with an axis of said hole, such that when inserted therein, said at least end portions of said plurality of elongated bristles are deflected in a direction towards an insertion end of said hole, at a deflection angle away from said original orientation; and attaching the tissue to said brush.

27. A method, according to claim 26, wherein:

said brush further includes a cloth strip attached thereto, said cloth strip having at least in part a widened dimension; and said step of attaching includes affixing the tissue to said cloth strip across said widened dimension.

28. A method, according to claim 26, wherein:

said brush further includes wires extending therefrom said wires being tapered at ends thereof to present sharpened ends, said wires having sufficient rigidity to permit a piercing of the tissue by the sharpened ends of said wires without requiring use of needles; and said step of attaching includes sewing said wires through the tissue.

29. A method, according to claim 26, wherein a composition of said bristles is a plastic selected from a group comprising polyester, nylon, polytetraflouroethylene, polyglycolic acid, and polylactide.

30. A method, according to claim 26, wherein a composition of said stem is a plastic selected from a group comprising polyester, nylon, polytetraflouroethylene, polyglycolic acid, and polylactide.

31. A method, according to claim 26, wherein a composition of said stem is a metal selected from a group comprising stainless steel, titanium, and tantalum.

32. A method, according to claim 26, wherein said brush is comprised entirely of a biodegradable plastic.

33. A method, according to claim 26, wherein:

said plurality of elongated bristles are sufficiently flexible to permit bending over at least a portion of lengths thereof such that when said brush is inserted into said hole, said plurality of elongated bristles are flexed and are deflected in said direction towards said insertion end of said hole.

34. A method for fixing a tissue to a bone, comprising the steps of:

providing a brush, said brush including a stem and a plurality of elongated bristles attached to said stem in a spaced apart manner over at least a portion of a length thereof, said plurality of elongated bristles arranged crosswise to said stem, an average distance between ends of opposed ones of said plurality of elongated bristles defining a brush diameter, said brush including means for resiliently permitting angular deflection of at least end portions of said plurality of elongated bristles away from an original orientation thereof said brush further includes a loop carried thereon;

boring a hole in the bone, said hole having a diameter less than said brush diameter and a depth sufficient to receive said brush substantially therein;

inserting said brush into said hole with said stem in substantial alignment with an axis of said hole, such that when inserted therein said at least end portions of said bristles are deflected in a direction towards an insertion end of said hole, at a deflection angle away from said original orientation; and attaching the tissue to said brush, which includes affixing the tissue to said loop.

35. A method for fixing a tissue to a bone, comprising of:

providing a brush, said brush including a stem and a plurality of elongated bristles attached to said stem in a spaced apart manner over at least a portion of a length thereof, said plurality of elongated bristles arranged crosswise to said stem, an average distance between ends of opposed ones of said plurality of elongated bristles defining a brush diameter said brush including means for resiliently permitting angular deflection of at least end portions of said plurality of elongated bristles away from an original orientation thereof;

boring a hole in the bone, said hole having a diameter less than said brush diameter and a depth sufficient to receive said brush substantially therein:

inserting said brush into said hole with said stem in substantial alignment with an axis of said hole, such that when inserted therein, said at least end portions of said bristles are deflected in a direction towards an insertion end of said hole, at a deflection angle away from said original orientation, said diameter of said hole being sized to angularly deflect said at least end portions of said plurality of elongated bristles at said deflection angle in a range from about 30° to about 60° when said brush is inserted therein: and attaching the tissue to said brush.

36. A method for fixing a tissue to a bone, comprising the steps of:

providing a brush, said brush including a stem and a plurality of elongated bristles attached to said stem in a spaced apart manner over at least a portion of a length thereof, said plurality of elongated bristles arranged crosswise to said stem, an average distance between ends of opposed ones of said plurality of elongated bristles defining a brush diameter, said brush including means for resiliently permitting angular deflection of at least end portions of said plurality of elongated bristles away from an original orientation thereof, at least a portion of said plurality of elongated bristles including concave end surfaces at free ends thereof;

boring a hole in the bone, said hole having a diameter less than said brush diameter and a depth sufficient to receive said brush substantially therein;

inserting said brush into said hole with said stem in substantial alignment with an axis of said hole, such that when inserted therein, said at least end portions of said bristles are deflected in a direction towards an insertion end of said hole, at a deflection angle away from said original orientation; and attaching the tissue to said brush.

37. A method for packaging a device for insertion into a vessel subject to bidirectional fluid flow for occlusion thereof, the method comprising the steps of:

providing a brush including first and second ends, said brush further including a stem and a plurality of elongated bristles attached in crosswise manner to said stem spaced apart over at least a portion of a length thereof, an average distance between ends of opposed ones of said plurality of elongated bristles defining a brush diameter, said brush diameter being larger than an internal diameter of the vessel, said brush further including means for permitting resilient angular deflection of at least end portions of said plurality of elongated bristles away from an original orientation thereof;

providing a tube having an internal diameter less than said brush diameter;

inserting said brush in a first direction entirely into said tube to deflect said at least end portions of said plurality of elongated bristles in a second direction opposite said first direction;

sliding said brush in said first direction until a first portion of said brush extends beyond said tube and a second portion of said brush remains within said tube, thereby returning the plurality of elongated bristles along said first portion to substantially said original orientation; and sliding said brush in said second direction until fully inserted within said tube to deflect said at least end portions of said plurality of elongated bristles along said first portion in said first direction.

38. A method according to claim 37, wherein said means for permitting resilient angular deflection of at least end portions of said plurality of elongated bristles includes forming said plurality of elongated bristles from a resilient material to permit bending thereof.

39. A method for fixing a tissue to a bone, comprising the steps of:

providing a brush, said brush including a stem and a plurality of elongated bristles attached to said stem in a spaced apart manner over at least a portion of a length thereof, said plurality of elongated bristles arranged crosswise to said stem and substantially perpendicular with said stem, an average distance between ends of opposed ones of said plurality of elongated bristles defining a brush diameter, said brush diameter being substantially greater than a thickness of said stem, said brush including means for permitting resilient angular deflection of at least end portions of said plurality of elongated bristles away from an original orientation thereof;

boring a hole in the bone, said hole having a diameter less than said brush diameter and a depth sufficient to receive said brush substantially therein;

inserting said brush into said hole with said stem in substantial alignment with an axis of said hole, said plurality of elongated bristles being sufficiently flexible to permit bending over at least a portion of lengths thereof such that when said brush is inserted into said hole, said plurality of elongated bristles are flexed and are deflected in said direction towards said insertion end of said hole at a deflection angle away from said original orientation; and attaching the tissue to said brush.

* * * * *